US012752045B2

(12) United States Patent
Yuds et al.

(10) Patent No.: US 12,752,045 B2
(45) Date of Patent: Oct. 6, 2026

(54) MEDICAL FLUID DRAIN CONTAINERS AND RELATED SYSTEMS AND METHODS

(71) Applicant: Fresenius Medical Care Holdings, Inc., Waltham, MA (US)

(72) Inventors: David Yuds, Hudson, NH (US); Jun Yi, Norman, OK (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 135 days.

(21) Appl. No.: 18/753,465

(22) Filed: Jun. 25, 2024

(65) Prior Publication Data

US 2024/0424179 A1 Dec. 26, 2024

Related U.S. Application Data

(62) Division of application No. 17/385,445, filed on Jul. 26, 2021, now Pat. No. 12,042,587.

(51) Int. Cl.

*A61M 1/16* (2006.01)
*A61M 1/00* (2006.01)
*A61M 1/28* (2006.01)

(52) U.S. Cl.

CPC ........ *A61M 1/1696* (2013.01); *A61M 1/1654* (2013.01); *A61M 1/168* (2013.01); *A61M 1/287* (2013.01); *A61M 1/67* (2021.05); *A61M 1/69* (2021.05)

(58) Field of Classification Search

CPC .... A61J 1/10; A61J 1/12; A61J 1/2024; A61J 1/2093; A61L 2/0047; A61L 2/10; A61M 1/1654; A61M 1/1668; A61M 1/1674; A61M 1/168; A61M 1/1696; A61M 1/287; A61M 1/67; A61M 1/69; C02F 1/32; C02F 1/66

See application file for complete search history.

(56) References Cited

U.S. PATENT DOCUMENTS 4,316,466 A * 2/1982 Babb .................. A61M 1/3672 604/35
6,267,242 B1 7/2001 Nagata et al.
9,399,090 B2 7/2016 Collier et al.
9,878,084 B2 1/2018 Simonis
2012/0310150 A1* 12/2012 Brandl ................ A61M 1/1656 604/410

(Continued)

FOREIGN PATENT DOCUMENTS

JP 2000-210682 8/2000
JP 2001-269670 10/2001
JP 2006-187683 7/2006

(Continued)

OTHER PUBLICATIONS

Heger, "What to Do if Your Septic Customer is on Dialysis," Jan. 23, 2017, retrieved on Oct. 19, 2021, retrieved from URL <https://www.onsiteinstaller.com/online_exclusives/2017/01/what_to_do_if your_septic_customer_is_on_dialysis>, 5 pages.

(Continued)

*Primary Examiner* — Dirk R Bass
(74) *Attorney, Agent, or Firm* — Fish & Richardson P.C.

(57) ABSTRACT

A method includes collecting used dialysis fluid in a container and combining the dialysis fluid with an acid to lower the pH value of the used dialysis fluid.

7 Claims, 5 Drawing Sheets

(56) References Cited

U.S. PATENT DOCUMENTS

| | | | |
|---|---|---|---|
| 2014/0158588 | A1 | 6/2014 | Pudil et al. |
| 2017/0290970 | A1 | 10/2017 | Friederichs et al. |

FOREIGN PATENT DOCUMENTS

| | | |
|---|---|---|
| JP | 2020-195997 | 12/2020 |
| JP | 2021-003262 | 1/2021 |
| JP | 2021-037467 | 3/2021 |

OTHER PUBLICATIONS

International Preliminary Report on Patentability in International Appln. No. PCT/US2022/037976, mailed Feb. 8, 2024, 11 pages.

International Search Report and Written Opinion in International Appln. No. PCT/US2022/037976, mailed Jan. 30, 2023, 19 pages.

Translation of JP 2021-003262, Furukawa et al., published Jan. 14, 2021, 6 pages.

* cited by examiner

MEDICAL FLUID DRAIN CONTAINERS AND RELATED SYSTEMS AND METHODS

CROSS-REFERENCE TO RELATED APPLICATIONS

This application is a divisional application of and claims the benefit of priority to U.S. application Ser. No. 17/385,445, filed on Jul. 26, 2021, the contents of which are hereby incorporated by reference.

TECHNICAL FIELD

The present disclosure relates to medical fluid drain containers and related systems and methods.

BACKGROUND

Dialysis is a treatment used to support a patient with insufficient renal function. The two principal dialysis methods are hemodialysis and peritoneal dialysis.

During hemodialysis ("HD"), the patient's blood is passed through a dialyzer of a dialysis machine while also passing a dialysis solution or dialysate through the dialyzer. A semi-permeable membrane in the dialyzer separates the blood from the dialysate within the dialyzer and allows diffusion and osmosis exchanges to take place between the dialysate and the blood stream. These exchanges across the membrane result in the removal of waste products, including solutes like urea and creatinine, from the blood. These exchanges also regulate the levels of other substances, such as sodium and water, in the blood. In this way, the dialysis machine acts as an artificial kidney for cleansing the blood.

During peritoneal dialysis ("PD"), a patient's peritoneal cavity is periodically infused with dialysis solution or dialysate. The membranous lining of the patient's peritoneum acts as a natural semi-permeable membrane that allows diffusion and osmosis exchanges to take place between the solution and the blood stream. These exchanges across the patient's peritoneum, like the continuous exchange across the dialyzer in HD, result in the removal of waste products, including solutes like urea and creatinine, from the blood, and regulate the levels of other substances, such as sodium and water, in the blood.

Many PD machines are designed to automatically infuse, dwell, and drain dialysate to and from the patient's peritoneal cavity. The treatment typically lasts for several hours, often beginning with an initial drain procedure to empty the peritoneal cavity of used or spent dialysate. The sequence then proceeds through the succession of fill, dwell, and drain phases that follow one after the other. Each phase is called a cycle.

SUMMARY OF THE INVENTION

In one aspect, a method includes collecting used dialysis fluid in a container and combining the dialysis fluid with an acid to lower the pH value of the used dialysis fluid.

In another aspect, a dialysis fluid drain container comprises a first compartment for collecting used dialysis fluid and an inlet configured to be connected to a used dialysis fluid line connected to the first compartment. The fluid drain container also comprises a second compartment containing an acid and an outlet configured to be connected to a drain line connected to the second compartment. Fluid transfer between the first compartment and the second compartment is prevented in a first state and permitted in a second state.

In yet another aspect, a box is configured to receive a used dialysis fluid container and emits ultraviolet waves directed at the used dialysis fluid container.

Embodiments can include one or more of the following features.

In some embodiments, the method comprises disposing of a mixture of the used dialysis fluid and the acid in a septic system.

In certain embodiments, the container is a bag.

In some embodiments, the container comprises a first chamber in which the used dialysis fluid is collected and a second chamber that contains the acid.

In certain embodiments, the acid is combined with the used dialysis fluid by manipulating the container.

In some embodiments, manipulating the container comprises applying pressure to the second chamber to add the acid to the dialysis fluid.

In certain embodiments, manipulating the container comprises adding pressure to the first chamber to add the acid to the dialysis fluid.

In some embodiments, the container further comprises a frangible region that separates the first chamber from the second chamber.

In certain embodiments, the acid is combined with the used dialysis fluid by introducing the acid into the container from an external source.

In some embodiments, the external source comprises a syringe.

In certain embodiments the acid comprises one of: citric acid, acetic acid, lactic acid, or muriatic acid.

In some embodiments, the used dialysis fluid comprises used peritoneal dialysis fluid.

In certain embodiments, the used dialysis fluid comprises used hemodialysis fluid.

In some embodiments, the container further comprises a frangible seal between the first compartment and the second compartment that is unbroken in the first state and broken in the second state.

In certain embodiments, the second compartment is a syringe.

In some embodiments, the syringe comprises a plunger that is cocked in the first state and depressed in the second state.

In some embodiments, the acid is a powder.

Embodiments can include one or more of the following advantages.

Generally, used dialysate is safe to dispose of in city sewer lines, but can be damaging to septic systems. The high pH value of used dialysate negatively impacts the beneficial microbes used in septic systems to treat wastewater. There also may be harmful bacteria in used dialysate that can negatively impact the septic system.

Certain dialysis fluid drain containers described herein enable a user to effectively lower the pH value of used dialysate so that disposing of the used dialysate in a septic system will not damage the septic system. In some cases, for example, an acid within the drain container can react with bases in the used dialysate to lower the pH value of the used dialysate.

Some of the systems described herein enable a user to disinfect the used dialysate so that disposing of the used dialysate in a septic system will not damage the septic system. In certain cases, for example, the systems include a UV box that kills bacteria that may be harmful to the septic system.

DETAILED DESCRIPTION

This disclosure relates generally to medical fluid drain bags (e.g., dialysis fluid drain bags) for collecting used medical fluid (e.g., used dialysate) to be disposed of after a medical treatment (e.g., a dialysis treatment). In some cases, a medical fluid pumping system (e.g., a dialysis system) includes a medical fluid pumping machine (e.g., a dialysis machine) having a medial fluid drain bag (e.g., a dialysis fluid drain bag) that is fluidly connected to a drain line of the system. The drain bag collects used medical fluid (e.g., used dialysate) throughout the treatment. The used medical fluid can be disposed of in a septic system after the treatment by being poured into a toilet, a bathtub, a sink, or any other plumbing fixture connected to the septic system via a drain.

Figure 1:
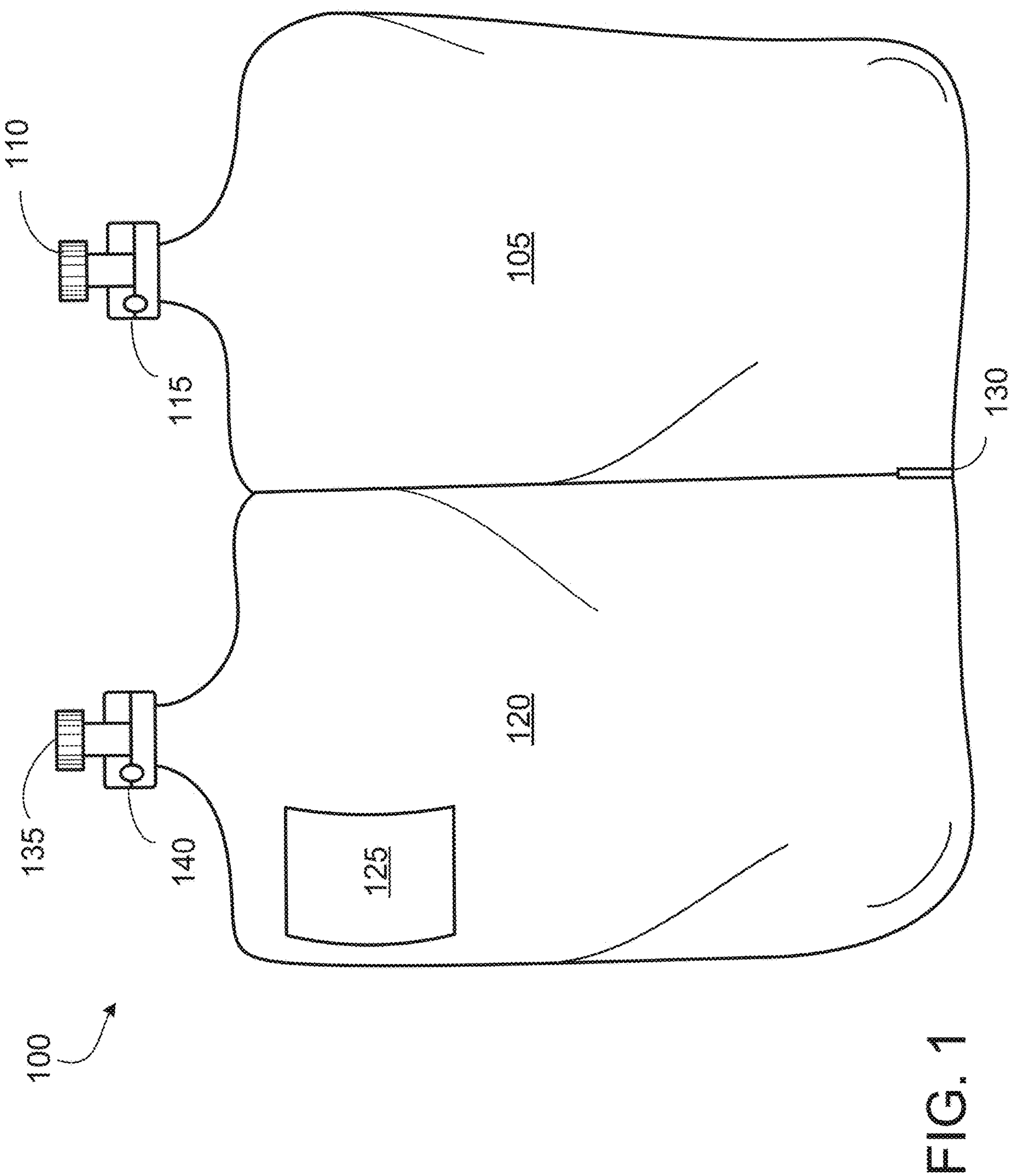
FIG. 1 is a schematic illustration of a dialysis fluid drain bag that includes citric acid to be mixed with used dialysate in the drain bag.

Referring to FIG. 1, a dialysis fluid drain bag 100 includes a first chamber 105 with an inlet 110 configured to be connected to a drain line of a PD system. The inlet 110 includes an inlet clamp 115 that can selectively open or close the inlet 110. The inlet 110 is sealed when the inlet clamp 115 is closed. The first chamber 105 collects used dialysate from the patient during a PD treatment.

The drain bag 100 also includes a second chamber 120 that contains a citric acid packet 125 that includes a water soluble package or casing containing citric acid. The citric acid can be in the form of a dry powder or citric acid concentrate. The citric acid packet 125 will mix with the used dialysate collected in the first chamber 105 to lower the pH value of the used dialysate.

In some embodiments, the citric acid packet 125 contains three grams of dry citric acid powder or an equivalent amount of citric acid concentrate (e.g., six milliliters of 50% citric acid concentrate, 12 milliliters of 25% citric acid concentrate, etc.). This is typically a sufficient amount of citric acid to lower the pH value of ten liters of used dialysate to a safe pH value for septic systems, e.g., below about 8 pH. As the volume of used dialysate increases, the amount and/or concentration of citric acid required to sufficiently lower the pH value of the used dialysate also generally increases. Similarly, as the volume of used dialysate decreases, the amount and/or concentration of citric acid required to sufficiently lower the pH value of the used dialysate also decreases.

The drain bag 100 also includes an outlet 135 connected to the second chamber 120. The outlet 135 includes an outlet clamp 140 that can selectively open or close the outlet 135. The outlet 135 is sealed when the outlet clamp 140 is closed.

The drain bag 100 includes a seal 130 in the form of a frangible member that initially prevents fluid transfer between the first chamber 105 and the second chamber 120, and thus prevents the used dialysate contained in the first chamber 105 from contacting the citric acid packet 125 in the second chamber 120. The seal 130 can be broken (e.g., by a patient) to permit such fluid transfer for purposes of mixing the used dialysate and the contents of the citric acid packet 125. In the illustrated embodiment, the patient does not need to introduce a foreign object (e.g., a needle) to break the seal 130. Rather, this may be accomplished by applying pressure to the first chamber 105, which in turn applies pressure to the seal 130. For example, the user can press his or her hand down on the liquid filled first chamber 105 to pressurize the chamber 105 and rupture the seal 130. The drain bag 100 can be configured to hold a volume of used dialysate that accumulates over the course of a typical PD treatment. In some cases, for example, the drain bag 100 is configured to hold ten liters of fluid.

Figure 2:
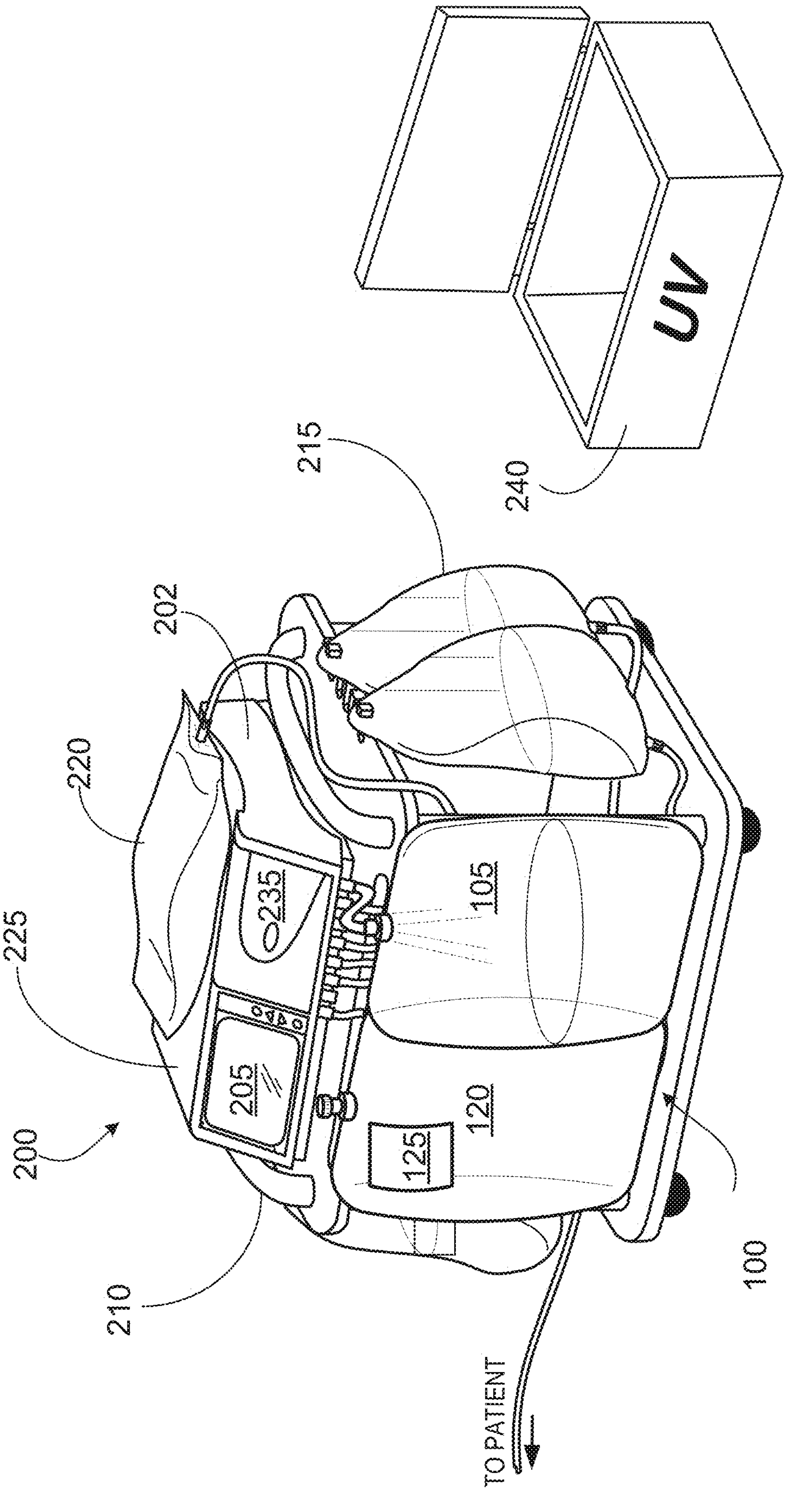
FIG. 2 is a perspective view of a PD system including a PD cycler, a disposable set including, among other components, the drain bag of FIG. 1 connected to the PD cycler, and an ultraviolet (UV) box.

FIG. 2 illustrates a PD system 200 including a PD cycler 202, a cart 210, four PD solution bags 215 and their associated tubing, a UV box 240, a disposable cassette (positioned behind a door 235 of the PD cycler 202) to direct fluids during treatment, and the drain bag 100. The cycler 202 includes a touch screen 205, forming the control panel for the user interface operated by the patient. The cycler 202 is seated on top of the cart 210, which is designed to accommodate the PD solution bags and associated tubing. The drain bag 100 is suspended from a finger on the front of the cart 210.

The PD solution bags 215 are suspended from fingers on the sides of the cart 210 as shown. A heater bag 220 is shown lying in a shallow concave depression forming a heater tray 225, which is sized and shaped to accommodate a typical five liter bag of PD solution. The heater tray 225 has a plurality of heating coils (not shown) embedded below the surface. A temperature sensor is positioned in the surface of the heater tray 225 to track the temperature of the solution in the heater bag for a thermostatic control circuit that turns the heating coils on and off as needed to maintain the PD solution at the desired temperature. The cassette is inserted into a cassette compartment formed between the hinged door 235 and the door 235 when the door is closed and securely latched. The drain bag 100 is attached to the drain line of PD cycler 202. Because the dialysis solution bags 215, the heater bag 220, the patient line, and the drain bag 100 are connected to the cassette, dialysis solution is allowed to flow into and out of the cassette during use.

Still referring to FIG. 2, the ultraviolet ("UV") box 240 is a container with a lid that can be opened and closed and emits a UV light within the container. The UV box 240 is used to disinfect the used dialysate within the drain bag 100, as will be described later.

Typical PD machines utilize six fluid-processing sequences: flush, prime, drain, fill, pause, and dwell. The purpose of the flush sequence is to remove air from all the lines (except the patient line) and from the cassette. This is accomplished by pumping dialysate solution through the lines to be flushed. The prime sequence removes air from the patient line by pumping dialysate solution from the heater bag through the patient line.

During PD treatment, the patient line is connected to a patients' abdomen via a catheter. The PD treatment typically begins by emptying the patient of spent dialysis solution that remains in the patient's abdomen from the previous treatment. To do this, the PD cycler is activated to draw the spent dialysis solution into the cassette from the patient. The spent dialysis solution is then pumped from the cassette to the drain bag 100 via the drain line.

After draining the spent dialysis solution from the patient, heated dialysis solution is transferred from the heater bag 220 to the patient. To do this, the PD cycler is activated to cause the warmed dialysis solution to be drawn into the cassette from the heater bag 220. The warmed dialysis solution is then pumped from the cassette to the patient via the patient line.

Once the dialysis solution has been pumped from the heater bag 220 to the patient, the dialysis solution is allowed to dwell within the patient for a period of time. During this dwell period, toxins cross the peritoneum of the patient into the dialysis solution from the patient's blood. As the dialysis solution dwells within the patient, the PD cycler 202 prepares a fresh dialysate to deliver to the patient in a subsequent cycle. In particular, the PD cycler 202 pumps fresh dialysis solution from one of the full dialysis solution bags 215 into the heater bag 220 for heating. To do this, the pump of the PD cycler is activated to draw the dialysis solution into the cassette from the selected dialysis solution bag 215. The dialysis solution is then pumped from the cassette to the heater bag 220.

After the dialysis solution has dwelled within the patient for the desired period of time, the spent dialysis solution is pumped from the patient to the drain bag 100. The heated dialysis solution is then pumped from the heater bag 220 to the patient where it dwells for a desired period of time. These steps are repeated with the dialysis solution from two of the three remaining dialysis solution bags 215. The dialysis solution from the last dialysis solution bag 215 is typically delivered to the patient and left in the patient until the subsequent PD treatment. The pause sequence allows the patient to disconnect from the machine once the patient has been filled with dialysate solution.

Once the treatment is finished and the patient is disconnected from the PD cycler 202, the inlet 110 is sealed by closing the inlet clamp 115 and the drain line is disconnected from the inlet 110 of the first chamber 105. The outlet 135 is already sealed by the outlet clamp 140, which remains closed.

With both clamps 115 and 140 closed, the seal 130 is broken by applying pressure to the first chamber 105 to allow the used dialysate to flow from the first chamber 105 to the second chamber 120.

After the seal 130 is broken, the used dialysate is allowed to flow from the first chamber 105 to the second chamber 120 and reach the citric acid packet 125. The citric acid packet 125 releases the citric acid when the water soluble casing dissolves in the used dialysate. The citric acid is allowed to mix with the used dialysate to lower the pH of the used dialysate.

The used dialysate contains a variety of bases, e.g., bicarbonate, phosphate, etc. The high number of bases in the used dialysate gives the used dialysate a high pH value because bases are high on the pH scale. Acids, such as citric acid, on the other hand, are low on the pH scale. When the citric acid reacts with the bases within the used dialysate, it lowers the overall pH value of the used dialysate.

Figure 3:
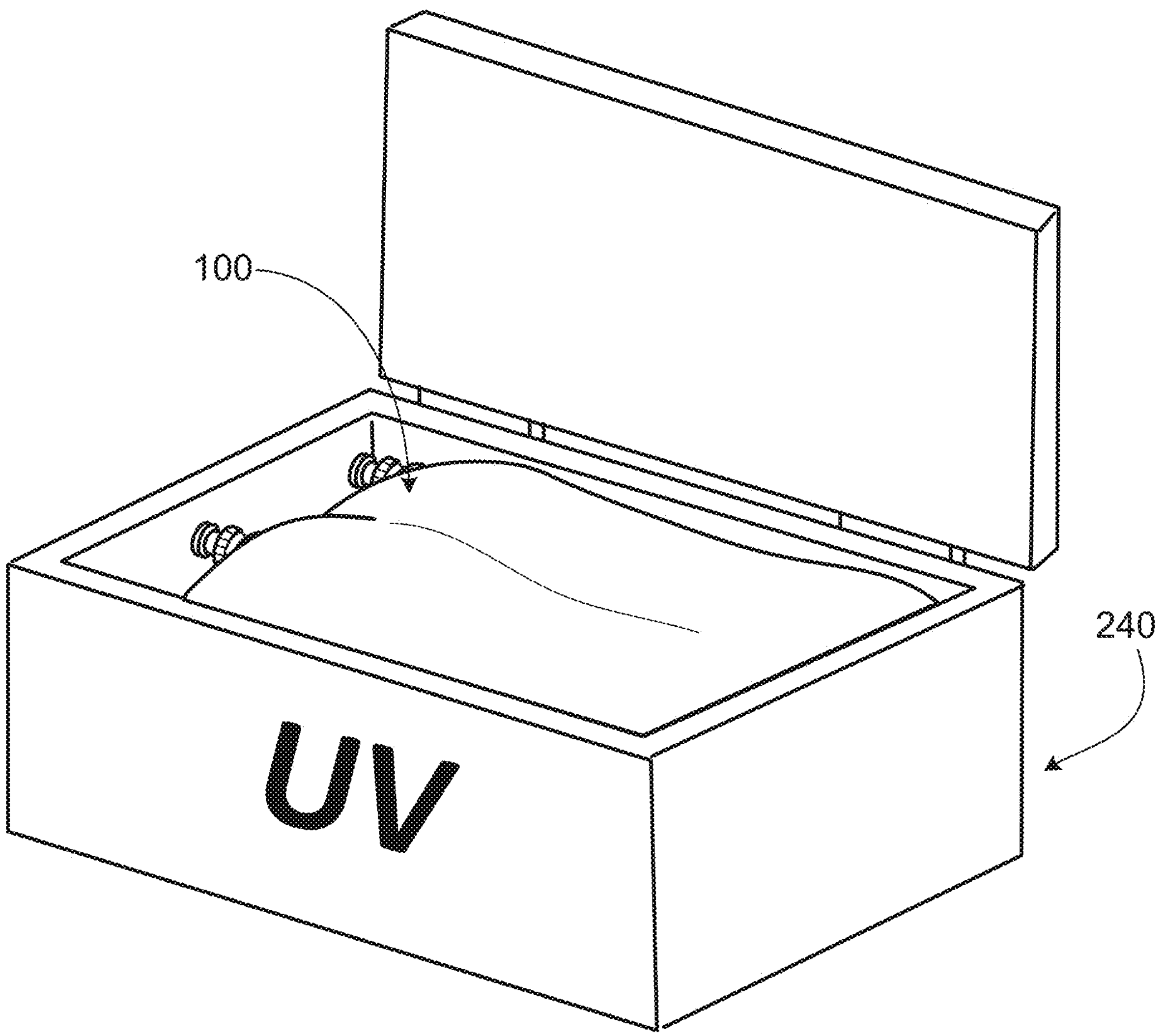
FIG. 3 is a perspective view of the UV box of FIG. 2 containing the drain bag of FIG. 1.

Once the citric acid has been introduced to the used dialysate, the drain bag 100 is placed into the UV box 240, as shown in FIG. 3, the lid of the UV box is closed, and the UV light is activated. In some cases, the drain bag 100 is left in the UV box 240 (with the UV light activated) for at least 30 minutes. Thirty minutes is typically a sufficient amount of time for the UV box 240 to disinfect the used dialysate and for the citric acid to mix with the used dialysate completely.

The UV box 240 disinfects the used dialysate by bombarding the used dialysate with waves in the ultraviolet range (e.g., 15 nanometers, 83 nanometers, 162 nanometers, 254 nanometers, 379 nanometers, etc.). Those skilled in the art will appreciate that UV waves of any length may be used alone or in concert with other wavelengths. The ultraviolet waves kills harmful bacteria that may be present in the used dialysate, thereby disinfecting the used dialysate.

Figure 4:
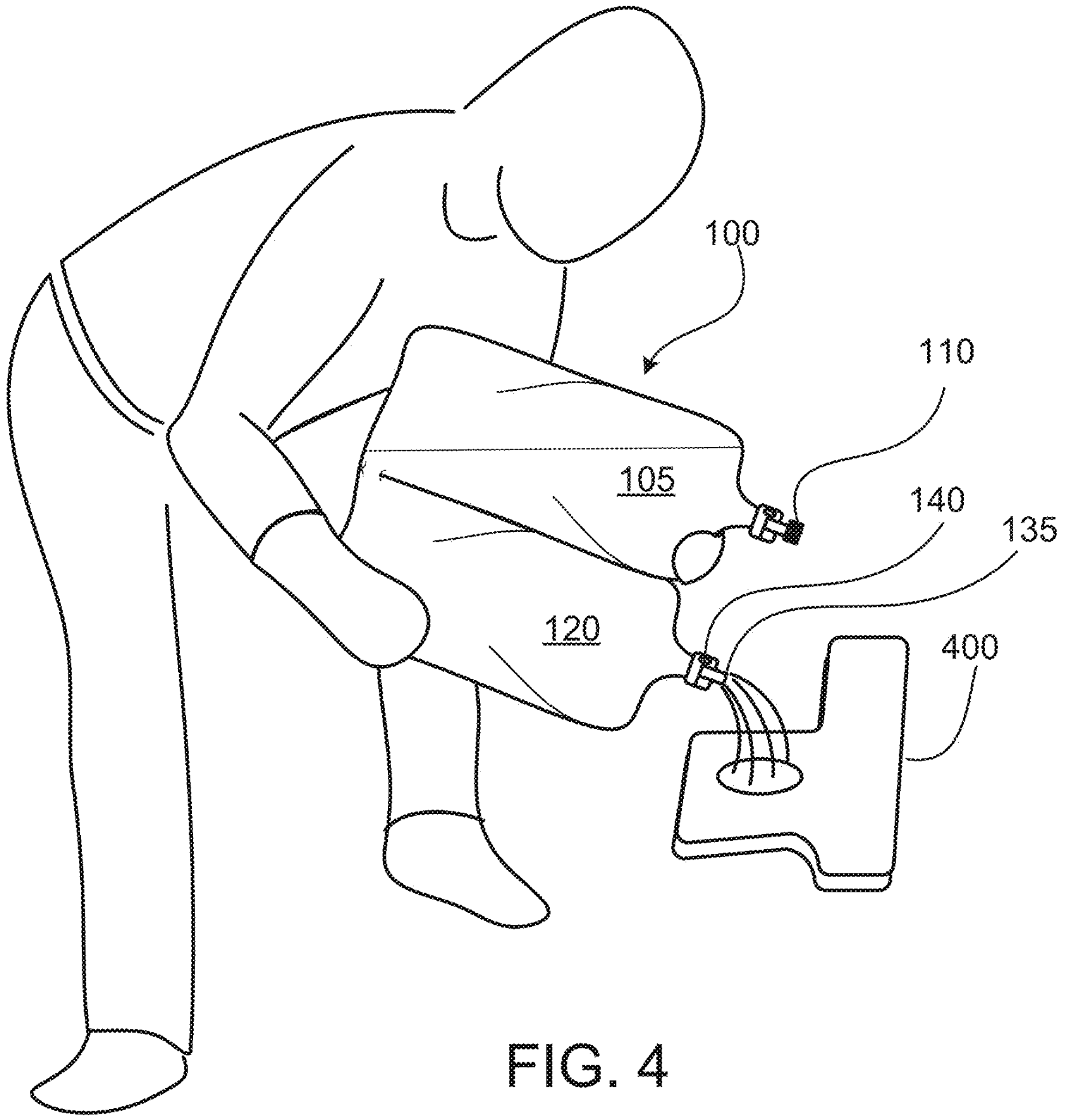
FIG. 4 is a perspective view of a user pouring used dialysate from the drain bag of FIG. 1 into a toilet connected to a septic system.

After the drain bag 100 has been in the UV box 240 for a desired amount of time, the drain bag 100 is removed from the UV box 240 and the used dialysate is poured into a toilet 400 that is connected to a septic system, as shown in FIG. 4. To dispose of the used dialysate, the outlet clamp 140 is opened to allow the used dialysate to flow out of the outlet 135 into the toilet 400. The user may also squeeze the drain bag 100 to increase the rate at which the used dialysate flows out of the drain bag 100.

The risk of damage to the septic system caused by the used dialysate is reduced because of the lowered pH value of the used dialysate. The disinfection process also makes the dialysate safer for septic systems by killing harmful bacteria within the used dialysate.

Figure 5:
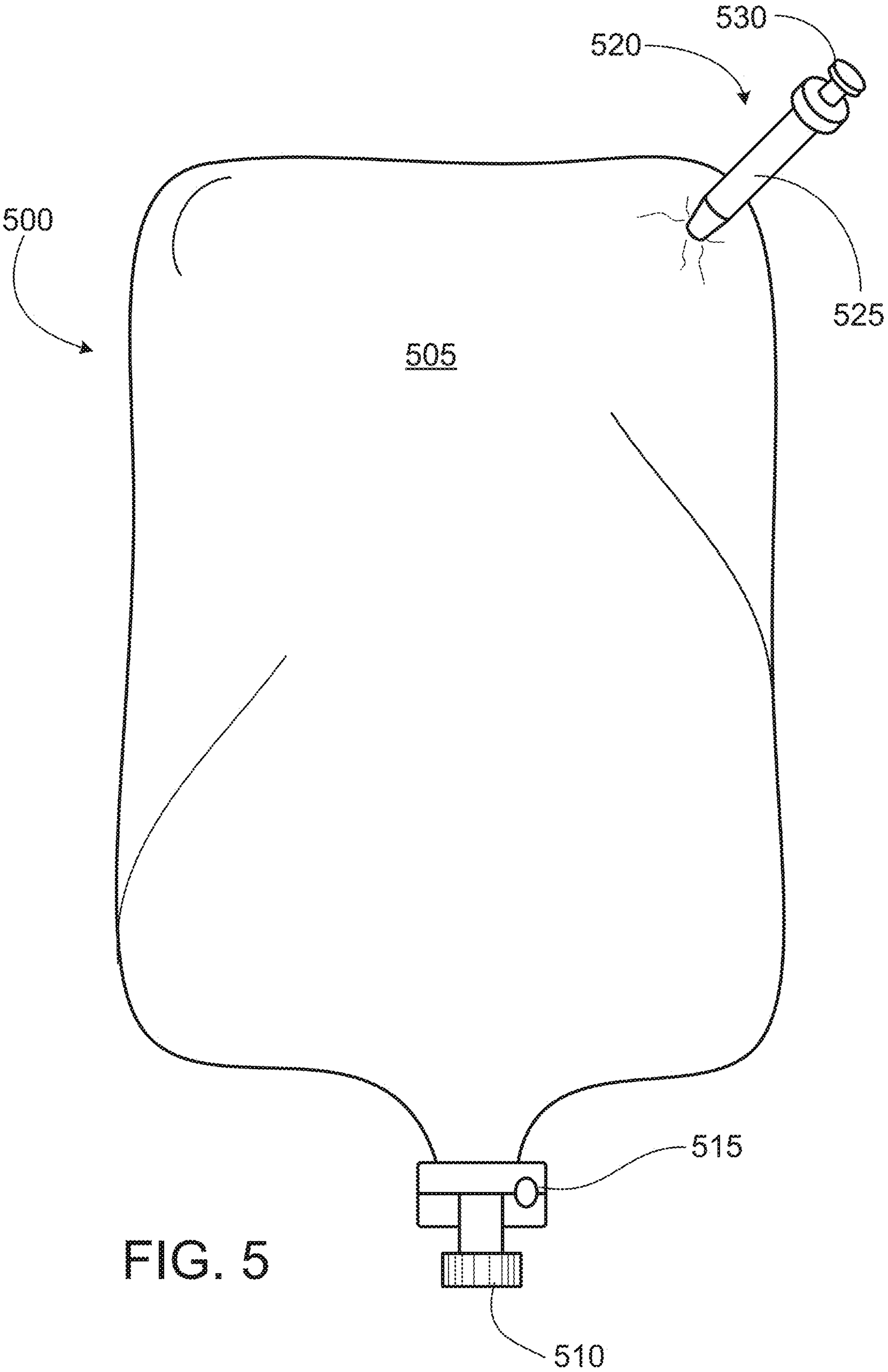
FIG. 5 illustrates another drain bag that includes a connector for connecting to a syringe to allow liquid citric acid concentrate to be injected into the drain bag for mixing with the used dialysate.

FIG. 5 illustrates an alternative drain bag 500 that can be used with the PD system 200 described above. The drain bag 500 has a chamber 505, which has an inlet 510 configured to be connected to a drain line of the PD system. The inlet 510 includes an inlet clamp 515 that can selectively open or close the inlet 510. The inlet 510 is open when the inlet clamp 515 is open, and the inlet 510 is sealed when the inlet clamp 515 is closed. The chamber 505 collects used dialysate from the PD system during treatment.

The drain bag 500 is connected to a syringe 520 containing citric acid concentrate 525. The syringe 520 has a plunger 530 that can be depressed to inject citric acid concentrate 525 into the chamber 505 of the drain bag 500. The syringe 520 contains six milliliters of 50% citric acid concentrate, or an equivalent amount of citric acid concentrate (e.g., 12 milliliters of 25% citric acid concentrate). This is typically a sufficient amount of citric acid to lower the pH value of ten liters of used dialysate to a safe pH value for septic systems, e.g., below about 8 pH.

The drain bag 500 can be used to collect used dialysate from a PD system as described above. Once the treatment is finished and the patient is disconnected from the PD cycler 202, the drain line is disconnected from the inlet 510 of the chamber 505. The inlet 510 is then sealed by closing the inlet clamp 515.

Once the inlet clamp 515 is closed, the plunger 530 of the syringe 520 is depressed to push the citric acid concentrate 525 into the first chamber 505. After the citric acid concentrate 525 is introduced, the used dialysate within drain bag 500 can be disinfected in the UV box 240 as described above.

To dispose of the disinfected dialysate, the inlet clamp 515 is opened to allow the used dialysate to flow out of the inlet 510 into a toilet. The used dialysate is safe to be disposed of in a toilet connected to a septic system.

While drain bags have been described, containers other than bags, such as boxes, barrels, etc., may alternatively be used to hold the used dialysate.

While the dialysis solution has been described as being pumped into the heater bag 220 from a single dialysis solution bag 215, dialysis solution can alternatively be pumped into the heater bag 220 from multiple dialysis solution bags 215. Such a technique may be advantageous, for example, when the dialysis solutions in the bags 215 have different concentrations (e.g., different dextrose concentrations) and a desired concentration for treatment is intermediate to the concentrations of the dialysis solution in two or more of the bags 215.

In certain embodiments, the seal 130 can be broken by directly applying pressure to the seal (e.g., squeezing, twisting, or manipulating the seal 130).

While the drain bags have been described as being ten liter drain bags, other sized bags or containers can be used. In some implementations, for example, the drain bag or container is configured to hold more than ten liters of fluid (e.g., ten liters, 15 liters, 20 liters, or more). If more used dialysate is collected in the drain bag, more citric acid can be used accordingly. In some implementations, the citric acid has a concentration of 50%, 60%, 70%, etc. and/or is provided in an amount of 12 milliliters, 15 milliliters, 18 milliliters, etc.

While the UV box has been described as a box, other containers that emit UV light, such as a UV drawer, can be used. In some implementations, the UV box can be a part of the cart. For example, the UV box can be a container that is attached to or integrally formed with the cart. In some implementations, the UV box can be a part of the PD cycler. For example, the UV box can be a container defined by the housing of the PD cycler or a drawer that retracts into a chamber defined by the housing of the PC cycler.

While the PD system 200 has been described as including the UV box 240, in some embodiments, systems do not include such a UV box. In some implementations, for example, the citric acid alone is sufficient to disinfect the used dialysate. In some embodiments, the citric acid packet may contain enough citric acid to lower the pH of the used dialysate and to also kill harmful bacteria that may be in the used dialysate. For example, a ten liter drain bag may contain 50 grams of dry citric acid powder or 100 milliliters of 50% citric acid concentrate. If more used dialysate is collected in the drain bag, more citric acid can be used accordingly. In some implementations, the citric acid has a concentration of 50%, 60%, 70%, etc. and/or is provided in an amount of 150 milliliters, 175 milliliters, 200 milliliters, etc.

While the citric acid packet 125 has been described as being water soluble, the citric acid can be released from the packet in other ways. For example, in other embodiments, the citric acid packet 125 may be breakable, wherein a patient can break the casing of the citric acid packet 125 to release the citric acid into the used dialysate. In some embodiments, a chunk of citric acid could be used without any package or casing.

While citric acid has been described to lower the pH of used dialysate, other acids may be used instead of or in addition to citric acid. In some cases, for example, acetic acid, lactic acid, muriatic acid, or other similar acids may be used.

While certain drain bags have been described above as having both an inlet and an outlet, in some embodiments both an inlet and outlet are not necessary. The drain compartments can alternatively have only one inlet that can also function as an outlet.

While the drain bags and containers above have been described as being part of PD systems, these types of drain bags can be used in any of various other types of medical fluid pumping systems. Other examples of medical fluid pumping systems in which the drain bags described herein can be used include hemodialysis systems, hemofiltration systems, and hemodiafiltration systems.

What is claimed is:

1. A dialysis fluid drain bag comprising:

a first compartment for collecting used dialysis fluid;

an inlet connected to the first compartment, the inlet configured to be connected to a used dialysis fluid line;

a second compartment containing an acid configured to change a pH value of the used dialysis fluid;

a frangible seal connecting the first compartment and the second compartment, wherein the frangible seal is configured to break and fluidly connect the first compartment to the second compartment when the dialysis fluid drain bag is manipulated; and an outlet connected to the second compartment, the outlet configured to be connected to a drain line;

wherein fluid transfer between the first compartment and the second compartment is prevented in a first state in which the frangible seal is unbroken and permitted in a second state in which the frangible seal is broken.

2. The bag of claim 1, wherein the frangible seal is configured to break when a user applies pressure to the first compartment.

3. The bag of claim 1, wherein the frangible seal is configured to break when a user manipulates the frangible seal.

4. The bag of claim 1, wherein the acid comprises a sufficient amount of acid to lower the pH value of ten liters of used dialysate below 8 pH.

5. The bag of claim 1, wherein the acid comprises one of: citric acid, acetic acid, lactic acid, or muriatic acid.

6. The bag of claim 5, wherein the acid is a powder.

7. The bag of claim 6, further comprising a water soluble packaging containing the acid.

* * * * *